(12) United States Patent
Seglke et al.

(10) Patent No.: US 7,463,982 B2
(45) Date of Patent: Dec. 9, 2008

(54) LIQUID CLASS PREDICTOR FOR LIQUID HANDLING OF COMPLEX MIXTURES

(75) Inventors: Brent W. Seglke, San Ramon, CA (US); Timothy P. Lekin, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 488 days.

(21) Appl. No.: 11/186,281

(22) Filed: Jul. 20, 2005

(65) Prior Publication Data
US 2006/0136150 A1 Jun. 22, 2006

Related U.S. Application Data

(60) Provisional application No. 60/638,722, filed on Dec. 22, 2004.

(51) Int. Cl.
*G01N 19/00* (2006.01)
(52) U.S. Cl. .............................. 702/25; 702/22; 702/23; 702/24; 436/55; 436/180; 422/62; 422/100
(58) Field of Classification Search ............. 702/22–25; 436/55, 180; 422/62, 100
See application file for complete search history.

(56) References Cited

U.S. PATENT DOCUMENTS

| | | |
|---|---|---|
| 5,597,457 A | 1/1997 | Craig et al. |
| 5,961,934 A | 10/1999 | Arnowitz et al. |
| 6,368,402 B2 | 4/2002 | DeTitta et al. |
| 6,608,883 B2 | 8/2003 | Olson et al. |
| 6,860,940 B2 | 3/2005 | Segelke et al. |
| 2002/0076818 A1* | 6/2002 | Vessey et al. ................. 436/55 |
| 2002/0141905 A1 | 10/2002 | Sha et al. |
| 2003/0150375 A1 | 8/2003 | Segelke et al. |
| 2004/0033181 A1 | 2/2004 | Segelke et al. |
| 2004/0141895 A1 | 7/2004 | Sha |

FOREIGN PATENT DOCUMENTS

| | | |
|---|---|---|
| EP | 1 191 312 A2 | 3/2002 |
| WO | WO 01/09595 A2 | 2/2001 |
| WO | WO 01/09595 A3 | 2/2001 |
| WO | WO 02/26342 A1 | 4/2002 |

OTHER PUBLICATIONS

Ward, K. B., et al., "Automatic Preparation of Protein Crystals Using Laboratory Robotics and Automated Visual Inspection," Journal of Crystal Growth 90 (1988) pp. 325-339.

* cited by examiner

*Primary Examiner*—Tung S Lau
*Assistant Examiner*—Sujoy K Kundu
(74) *Attorney, Agent, or Firm*—Eddie E. Scott; John H. Lee

(57) ABSTRACT

A method of establishing liquid classes of complex mixtures for liquid handling equipment. The mixtures are composed of components and the equipment has equipment parameters. The first step comprises preparing a response curve for the components. The next step comprises using the response curve to prepare a response indicator for the mixtures. The next step comprises deriving a model that relates the components and the mixtures to establish the liquid classes.

11 Claims, 3 Drawing Sheets

LIQUID CLASS PREDICTOR FOR LIQUID HANDLING OF COMPLEX MIXTURES

CROSS-REFERENCE TO RELATED APPLICATIONS

This application claims the benefit of U.S. Provisional Patent Application No. 60/638,722 filed Dec. 22, 2004 and titled "Liquid Class Predictor for Liquid Handling of Complex Mixtures." U.S. Provisional Patent Application No. 60/638,722 filed Dec. 22, 2004 and titled "Liquid Class Predictor for Liquid Handling of Complex Mixtures" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to liquid handling and more particularly to a liquid class predictor for liquid handling of complex mixtures.

2. State of Technology

United States Patent Application No. 2002/0076818 by Andrew R. Vessey, Gregory L. Porter, and Peter T. Siesel, titled "System and Method for Liquid Handling Parameters Optimization," published Jun. 20, 2002, provides the following state of technology information: "Liquid-handling equipment has always been important to biomedical research and life science applications. Pipettes need to be accurate and resist contamination, but still work quickly and efficiently in repetitive procedures. Although pipettes remain a key component of experimental protocols, new types of large-scale research require more automation and miniaturization in liquid handling capabilities. The Human Genome Project and combinatorial chemistry experiments are sending new chemical compounds into the drug discovery and development pipeline. There is an increasing need to handle larger numbers of compounds dissolved in liquids and a diversity of assays to adequately measure them. Pharmaceutical firms need to be able to accelerate the screening of chemical compounds for potential drug activity, such as enzyme-inhibition or receptor binding. The liquid-handling needs of pharmaceutical companies include diluting and moving test samples from plate to plate. Small amounts of samples need to be transferred to secondary plates that contain as little as one µl or less of liquid, and then conduct biochemical assays. The trend in drug discovery research is to screen compounds using 384-well plates. Pipettes have evolved to diverse devices that may be electronic, multi-channel, automated or robotic. They are typically slender and light, have thermal insulation, preset volumes, built-in tip ejectors, and mechanisms to program the devices to repeatedly deliver the same volume. Robotic systems perform the highly repetitive task of liquid handling and can be programmed to pipette, dilute, dispense, heat, cool, wash plates, and transfer liquids. Robotic systems also provide an audit trail, tracking and recording every step of the process. One of the most important benefits of automated liquid-handling is the precision and reproducibility of assays. The automated liquid-handling equipment today can be better utilized by applying Design of Experiments (DOE) techniques."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a liquid class predictor system for predicting the "liquid class" of a complex mixture of liquids from knowledge of the behavior of individual components in the mixture. The liquid class predictor system allows liquid handling machines to use mixtures with a wide range of viscosities and be dispensed with high precision. The liquid class predictor system can be used for any process for which high precision dispensing of liquids over a wide range of viscosities is required.

The performance of most liquid handling equipment is highly sensitive to the physical properties of liquids being handled and must be carefully calibrated to maintain precision. Machine calibration becomes impractical if the number of reagents becomes very large. Tuning instrument performance and assigning the correct machine parameters for each complex mixture of reagents generated from combinatorial matrices of liquids quickly becomes prohibitive given the number of possible combinations in complex mixtures.

One embodiment of the present invention provides an apparatus for establishing liquid classes of complex liquid mixtures for liquid handling equipment comprising a recipe mixer, a liquid class predictor, and a machine control system. The recipe mixer produces specific recipes of the complex liquid mixtures that will be used in the liquid handling equipment. The liquid class predictor determines the liquid classes of said specific recipes produced by said recipe mixer and produces liquid class information. The liquid class predictor provides the liquid class information to the machine control system.

Another embodiment of the present invention provides a method for establishing liquid classes of complex liquid mixtures for liquid handling equipment comprising the steps of mixing individual recipes of the complex liquid mixtures, predicting liquid classes of the complex liquid mixtures, and using the predicted liquid classes to instruct the liquid handling equipment.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
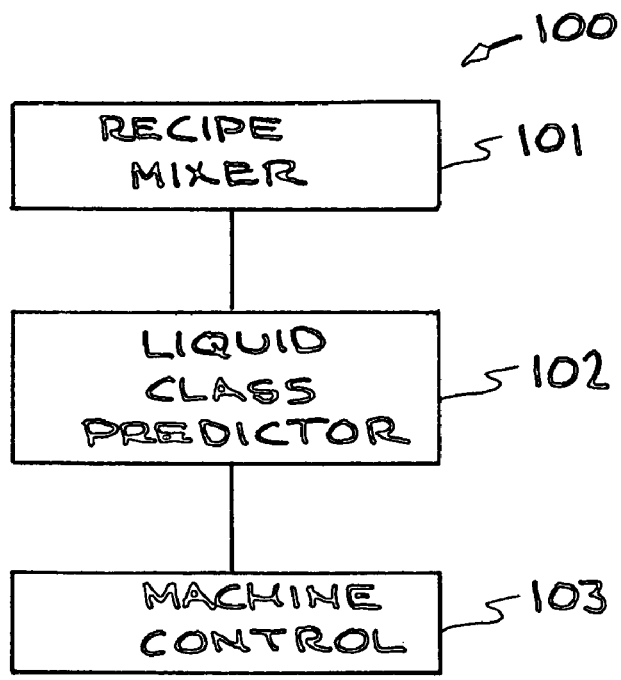
FIG. 1 illustrates one embodiment of a liquid class predictor system for establishing liquid classes of complex mixtures for liquid handling equipment constructed in accordance with the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, a liquid class predictor system for establishing liquid classes of complex mixtures for liquid handling equipment is illustrated. The liquid class predictor system is designated generally by the reference numeral 100. The liquid class predictor system 100 comprises a recipe mixer 101, a liquid class predictor 102, and a machine control system 103. The liquid class predictor system 100 provides a system for predicting the "liquid class" of a complex mixture of liquids from knowledge of the behavior of individual components in the mixture. The liquid class predictor system enables the use of complex mixtures of liquids by liquid handling equipment.

The recipe mixer 101 produces specific recipes of liquids that will be used in an individual liquid handling machine. The recipe mixer 101 provides the specific recipe for a complex liquid. Once produced, information about the recipes will be supplied to the liquid class predictor 102. Machines for mixing recipes are known. For example, a line of automated equipment is available from PerkinElmer, 45 William Street, Wellesley, Mass. 02481-4078, USA. The line of equipment includes the MultiPROBE II HT® system that will produce specific recipes of liquids for use in individual liquid handling machines.

The liquid class predictor 102 determines the liquid class of the specific recipe. The liquid class predictor 102 derives a model that relates the components of the mixtures and establish liquid classes for the recipes produced by the recipe mixer 101. Once the liquid class predictor 102 determines the liquid class for the specific recipes, the liquid class information is provided to the machine control system 103. Liquid classes are known in the art. For example, a description of the term "Liquid Class" is provided in United States Patent Application No. 2002/0076818 by Andrew R. Vessey, Gregory L. Porter, and Peter T. Siesel, titled "System and Method for Liquid Handling Parameters Optimization," published Jun. 20, 2002, which introduces a "liquid class" to arrange and describe the parameters needed for the accurate pipetting of a type of liquid using liquid-handling instruments. Each type of liquid that is used in an instrument requires a corresponding liquid class to ensure accurate pipetting of that liquid. The pipetting control software comes with a default set of liquid classes already defined for the following liquid types: dimethylsulfoxide (DMSO), ethanol, serum, water, water on liquid level, micro DMSO, micro priming liquid and micro water (the last three liquid types are used only if the instrument has the required nanopipetting hardware). The disclosure of United States Patent Application No. 2002/0076818 by Andrew R. Vessey, Gregory L. Porter, and Peter T. Siesel, titled "System and Method for Liquid Handling Parameters Optimization," published Jun. 20, 2002, is incorporated herein by reference.

The machine control system 103 enables the liquid handling machine to adjust for the complex mixture represented by the specific recipe. This allows the liquid handling machine to use mixtures with a wide range of viscosities so they can be dispensed with high precision. The liquid class predictor system 100 can be used for any process for which high precision dispensing of liquids over a wide range of viscosities is required. The performance of most liquid handling equipment is highly sensitive to the physical properties of liquids being handled and must be carefully calibrated for each "liquid class" to maintain precision. Machine calibration is a manageable task for a modest number of liquids or simple reagents but becomes impractical if the number of reagents becomes very large. Tuning instrument performance and assigning the correct machine parameters for each complex mixture of reagents generated from combinatorial matrices of liquids quickly becomes prohibitive given the number of possible combinations in complex mixtures. Liquid handling machines are known. For example, the Genesis® and MiniPrep® liquid-handling instrument series is available from TECAN, Tecan Group Ltd., Seestrasse 103, CH-8708 Maennedorf, Switzerland. Another example of liquid handling equipment is the Hydra® liquid handling equipment available from Matrix Technologies Corporation, 22 Friars Drive, Hudson, N.H. 03051, USA. Another example of a line of liquid handling equipment is available from Innovadyne Technologies, Inc., 2835 Duke Court, P.O. Box 7329, Santa Rosa, Calif. 95407-7329.

Referring again to FIG. 1, the liquid class predictor 100 is illustrated as apparatus for providing individual recipes of complex mixtures of liquids for liquid handling machines designated by the reference numeral 101, a liquid class predictor designated by the reference numeral 102, and a machine control system designated by the reference numeral 103. The machine parameters are chosen to optimize dispensing precision and accuracy. From a large number of recipes, groups of complex liquid mixtures can be constructed that belong to specific "liquid classes." The liquid classes result in the machine parameters delivering the desired precision and accuracy. The number of "liquid classes" must be significantly less than the number of individual components included in the complex liquid mixture. For example, the total number of liquid classes predicted to be sufficient for <5% cv across the whole range of usable viscosities with an Innovadyne corporation nano-dispensing robot is five.

The recipe mixer 101 produces a specific recipe for a complex liquid that will be used in an individual liquid handling machine. The recipe mixer 101 provides a specific "working mixed cocktail" made from reagents with known response curves. Based on the estimate of 5 liquid classes required for an Innovaydne instrument for example, 625 combinations of reagents would be sufficient to characterize all the combinations of liquid classes for protein crystallization compared to >3×10^6 possible combinations of individual reagents. The recipe mixer 101 provides the specific recipe for a complex liquid to the liquid class predictor 102.

The liquid class predictor 102 determines the liquid class of the specific recipe. The liquid class predictor 102 establishes liquid classes of complex mixtures wherein the mixtures are composed of components. The liquid handling equipment has specific parameters. The liquid class predictor 100 maps the characteristics for any of the practically infinite number of complex mixtures in to an appropriate liquid class with predetermined machine parameters. The liquid class predictor 100 incorporates a procedure and algorithm, implemented via software, assigning machine parameters for liquid handling instrumentation.

Once the liquid class predictor 102 determines the liquid class for the specific recipe, the class information is provided to the machine control system 103. The machine control system 103 enables the liquid handling machine to adjust for the complex mixture represented by the specific recipe. This allows the liquid handling machine to use mixtures with a wide range of viscosities so they can be dispensed with high precision. The liquid class predictor system 100 can be used for any process for which high precision dispensing of liquids over a wide range of viscosities is required. The performance of most liquid handling equipment is highly sensitive to the physical properties of liquids being handled and must be carefully calibrated for each "liquid class" to maintain precision. Tuning instrument performance and assigning the correct machine parameters for each complex mixture of reagents generated from combinatorial matrices of liquids quickly becomes prohibitive given the number of possible combinations in complex mixtures.

Figure 2:
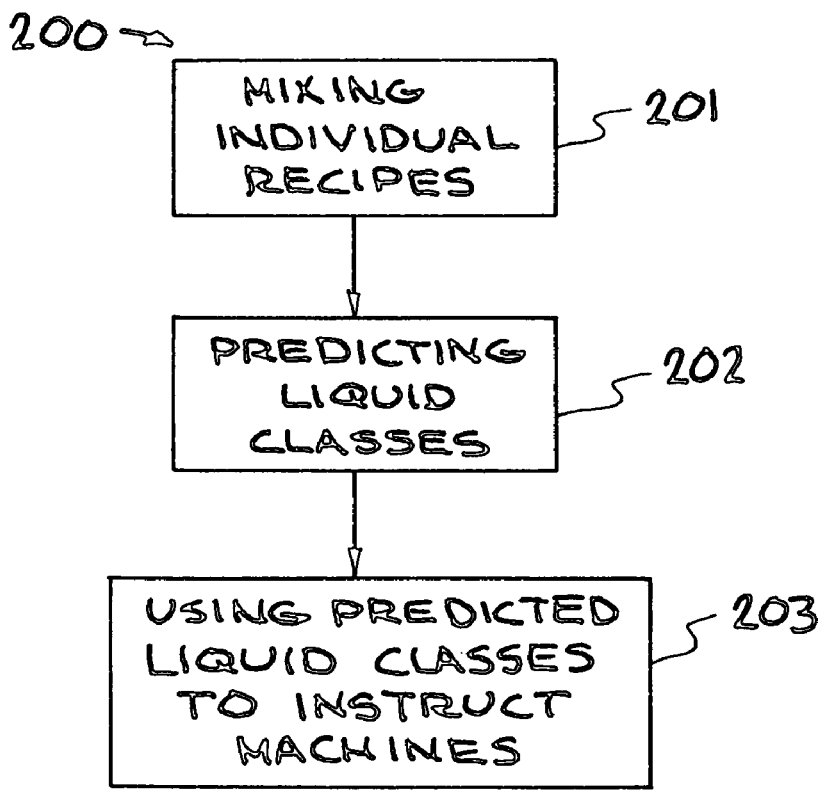
FIG. 2 illustrates one embodiment of a liquid class predictor method for establishing liquid classes of complex mixtures for liquid handling equipment.

Referring now to FIG. 2, a liquid class predictor method for establishing liquid classes of complex mixtures for liquid handling equipment is illustrated. The liquid class predictor method is designated generally by the reference numeral 200. The liquid class predictor method 200 comprises the steps of mixing individual recipes 201, predicting liquid classes 202 of the individual recipes, and using predicted liquid classes to instruct machines 203. The liquid class predictor method 200 provides for predicting the "liquid classes" of complex mixtures of reagents from knowledge of the viscosity or viscosity related behavior of individual components in the mixture. The liquid class predictor method enables the liquid handling of complex mixtures of reagents such that reagent mixtures with a wide range of viscosities can be dispensed with high precision. The liquid class predictor method 200 enables high throughput combinatorial screening with complex mixtures of reagents with diverse properties. The liquid class predictor method 200 has use with a broad range of liquid handling systems.

Step 201: Mixing Individual Recipes—In step 201, individual recipes are produced. The step of mixing individual recipes 201 produces specific recipes for complex liquids that will be used in liquid handling machines. The performance of most liquid handling equipment is highly sensitive to the physical properties of liquids being handled and must be carefully calibrated for each recipe. Machine calibration is a manageable task for a modest number of liquids or simple reagents but becomes impractical if the number of reagents becomes very large. Tuning instrument performance and assigning the correct machine parameters for each recipe of complex mixtures of reagents becomes prohibitive given the number of possible combinations in complex mixtures.

Step 202: Predicting Liquid Classes—The step of predicting liquid classes 202 determines the liquid classes of the individual recipes. Liquid classes are known in the art. For example, one description of the term "Liquid Class" is provided in United States Patent Application No. 2002/0076818 by Andrew R. Vessey, Gregory L. Porter, and Peter T. Siesel, titled "System and Method for Liquid Handling Parameters Optimization," published Jun. 20, 2002, which describes "Liquid class" as follows: "the concept of a "liquid class" to arrange and describe the parameters needed for the accurate pipetting of a type of liquid using liquid-handling instruments, such as the Genesis and MiniPrep liquid-handling instrument series available from TECAN, US, Inc. Each type of liquid that is used in an instrument requires a corresponding liquid class to ensure accurate pipetting of that liquid. The pipetting control software comes with a default set of liquid classes already defined for the following liquid types: dimethylsulfoxide (DMSO), ethanol, serum, water, water on liquid level, micro DMSO, micro priming liquid and micro water (the last three liquid types are used only if the instrument has the required nanopipetting hardware)." The disclosure of United States Patent Application No. 2002/0076818 by Andrew R. Vessey, Gregory L. Porter, and Peter T. Siesel, titled "System and Method for Liquid Handling Parameters Optimization," published Jun. 20, 2002, is incorporated herein by reference.

In step 202, predicting liquid classes, a "response curve" is made for each individual reagent that may make up a part of the complex recipe mixture. To construct the response curve the volume dispensed (or relative volume dispensed) vs. expected volume of water dispensed with a fixed set of machine parameters are measured. The machine parameters for any one data point are chosen to optimize dispensing precision—accuracy can be adjusted. The measurements are repeated over a range of volumes and concentration dispensed. The density of data is sufficient to ensure that interpolated points can be predicted within the desired precision. From the whole set of reagents groups of reagents can be constructed that belong to "liquid classes."

The number of liquid classes is sufficient to ensure that every reagent belongs to a liquid class that maps on to machine parameters that deliver the desired precision. The number of "liquid classes" must be significantly less than the number of reagents. For example, the total number of liquid classes predicted to be sufficient for <5% cv across the whole range of usable viscosities with an Innovadyne corporation nano-dispensing robot has been determined as five.

A "working set" of mixed cocktails is made from reagents with known response curves and the volume dispensed vs. expected volume of water dispensed with the same machine parameters is measured. The number of data points should be sufficient to over sample every combination of liquid class, which will be substantially less than the number of combinations of reagents. Based on the estimate of 5 liquid classes required for an Innovaydne instrument for example, 625 combinations of reagents would be sufficient to characterize all the combinations of liquid classes for protein crystallization compared to $>3 \times 10^6$ combinations of individual reagents.

Deriving a model that relates the components and the mixtures to establish the liquid classes. This comprises empirically deriving by linear regression a model that relates the liquid class of component and quantities of components of any complex mixture to the liquid class of the whole mixture. This derived model is the liquid. class predictor The liquid class predictor does not need to be a linear combination model, nor does it need to be empirically derived. It may be that liquid class can be directly inferred from viscosity for some instruments, for example, and a model can be derived from literature sources providing viscosity measurements. A predictor may also be generated by other computational means, like neural networks or genetic algorithms for instance.

Step 203: Using Predicted Liquid Classes to Instruct Machines—Once the liquid classes have been determined, the liquid class information is used in the step 203 of using the predicted liquid classes to instruct machines. The information is provided to the machine's control system. The machine control system enables the liquid handling machine to adjust for the complex mixture represented by the specific recipe. This allows the liquid handling machine to use mixtures with a wide range of viscosities so they can be dispensed with high precision. The liquid class predictor method 200 can be used for any process for which high precision dispensing of liquids over a wide range of viscosities is required. The performance of most liquid handling equipment is highly sensitive to the physical properties of liquids being handled and must be carefully calibrated for each "liquid class" to maintain precision. Machine calibration is a manageable task for a modest number of liquids or simple reagents but becomes impractical if the number of reagents becomes very large. Tuning instrument performance and assigning the correct machine parameters for each complex mixture of reagents generated from combinatorial matrices of liquids quickly becomes prohibitive given the number of possible combinations in complex mixtures.

One important use of the liquid class predictor method 200 is for instrumentation companies that produce robotic instruments for combinatorial screening, be it for protein crystallization or drug screening for new pharmaceuticals. For example, the liquid class predictor method 200 n has particular utility for applications in protein crystallography. Pharmaceutical companies are more and more moving in to high throughput protein crystallography (structural genomics) for drug development. Deducing protein structure is recognized as "a key element for drug discovery" as stated in *The Scientist*, Jan. 19, 2004. Given structural information derived from crystallography studies, scientists can design molecules that will bind in the active site of target proteins using computer aided modeling. Arriving at this point still requires a lot of effort to produce protein crystals and therefore methods development in protein crystallization is currently of pressing importance. Equally important is the likely use of the present invention for basic research. Protein crystallography research is still overwhelming carried out in publicly supported research labs. The present invention can be used for any process for which high precision dispensing of liquids over a wide range of viscosities is required.

Many factors come into play when aspirating and dispensing fluids. The factors include pump mechanics, tubing, aspirate, dispense speeds, air-gaps that separate the sample from the method fluid. In addition, characteristics of the fluid itself are important (i.e., viscosity, surface tension, and compressibility). The liquid class predictor method of the present invention maps the characteristics for any of a practically infinite number of complex mixtures into an appropriate liquid class with predetermined machine parameters.

Figure 3:
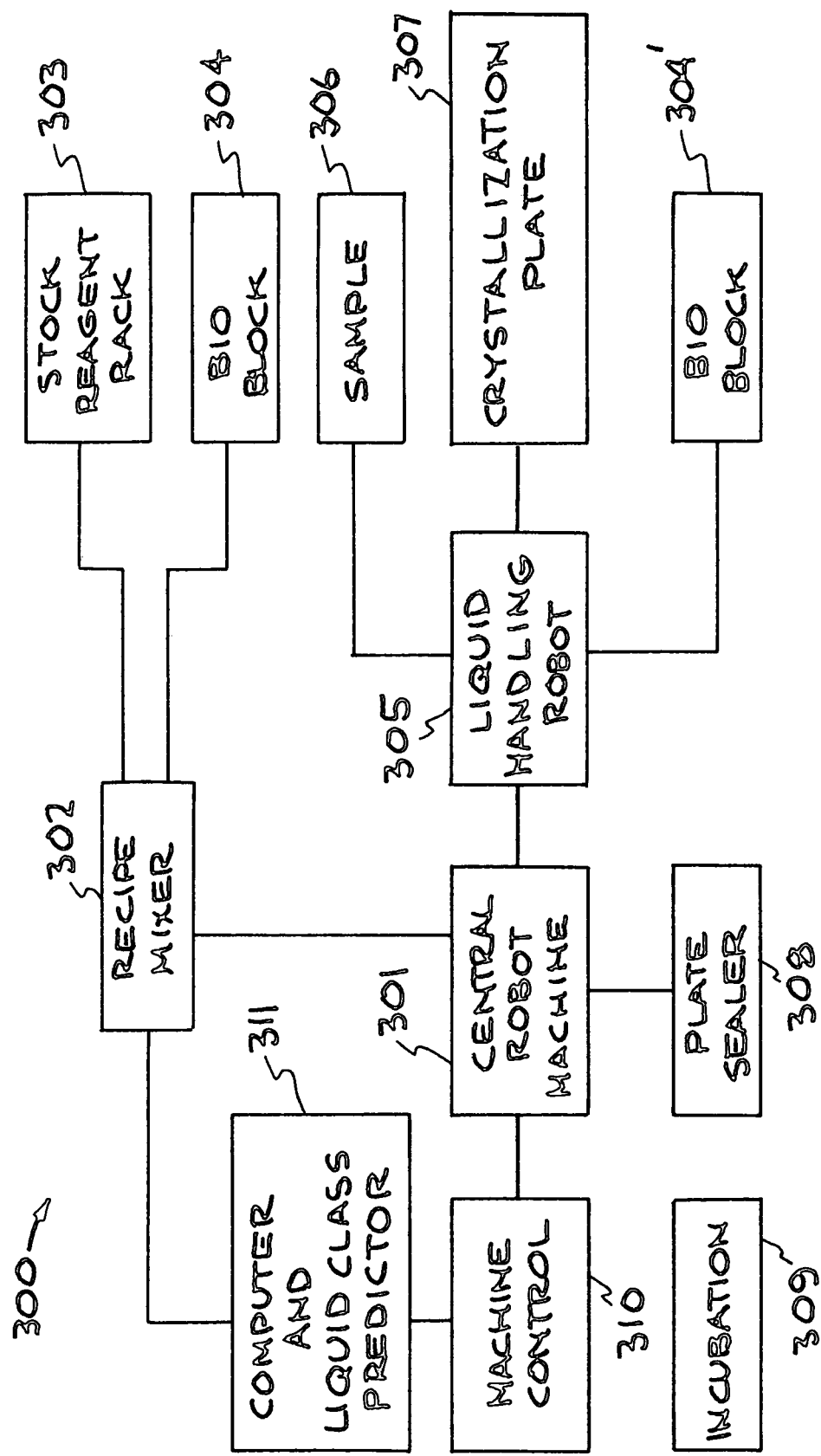
FIG. 3 illustrates another embodiment of a liquid class predictor system for establishing liquid classes of complex mixtures for liquid handling equipment constructed in accordance with the present invention.

Referring now to FIG. 3, another embodiment of a liquid class predictor system for establishing liquid classes of complex mixtures for liquid handling equipment constructed in accordance with the present invention is illustrated. This embodiment of a liquid class predictor system is part of an automated system for sustainable high-throughput crystallization screening. The automated system for sustainable high-throughput crystallization screening is designated generally by the reference numeral 300.

The automated system for sustainable high-throughput crystallization screening 300 was developed to generate fully customizable random screens of arbitrary numbers of crystallization experiments from premixed stock reagents. Components of the automated system for sustainable high-throughput crystallization screening system 300 include: a central robot machine 301; a recipe mixer 302; a stock reagent rack 303; a bio block 304; a liquid handling robot 305; a sample container 306; a crystallization plate 307; a plate sealer robot 308; an incubator unit 309; a camera 310; and a computer and liquid class predictor 311.

The central robot machine 301 moves the bio block 304 containing the recipes of reagents and the sample 306 to the crystallization plate 307. The central robot machine 301 handles recipe mixtures with a wide range of viscosities. The performance of most liquid handling equipment is highly sensitive to the physical properties of liquids being handled and must be carefully calibrated to maintain precision. Machine calibration becomes impractical if the number of reagents becomes very large as in the automated system for sustainable high-throughput crystallization screening 300. Tuning instrument performance and assigning the correct machine parameters for each complex mixture of reagents generated from combinatorial matrices of liquids quickly becomes prohibitive given the number of possible combinations in complex mixtures.

The machine control system 310 is connected to the computer and liquid class predictor 311 and the central robot machine 301. The machine control system 310 enables the central robot machine 301 to adjust for the complex mixture represented by the specific recipe. This allows the central robot machine 301 to use recipe mixtures with a wide range of viscosities so they can be dispensed with high precision.

The computer and liquid class predictor 311 determines the liquid class of the each specific recipe produced by the recipe mixer 302. The computer and liquid class predictor 311 establishes liquid classes of complex mixtures wherein the mixtures are composed of components. Liquid handling equipment generally have specific parameters. The computer and liquid class predictor 311 maps the characteristics for any of the practically infinite number of complex mixtures in to an appropriate liquid class with predetermined machine parameters. The computer and liquid class predictor 311 incorporates a procedure and algorithm, implemented via software, assigning machine parameters for liquid handling instrumentation.

Once the computer and liquid class predictor 311 determines the liquid class for each specific recipe, the class information is provided to the machine control system 310. The machine control system 310 enables the central robot machine 301 to adjust for the complex mixture represented by the specific recipes. This allows the central robot machine 301 to use mixtures with a wide range of viscosities so they can be dispensed with high precision.

The recipe mixer 302 produces specific recipes of complex liquids that will ultimately be placed in the crystallization plate 307. The recipe mixer 101 provides a specific "working mixed cocktail" made from reagents with known response curves. Based on the estimate of 5 liquid classes required for an Innovaydne instrument for example, 625 combinations of reagents would be sufficient to characterize all the combinations of liquid classes for protein crystallography compared to $>3 \times 10^6$ combinations of individual reagents. The recipe mixer 302 provides the specific recipe of complex liquids that will ultimately placed in the crystallization plate 307.

The stock reagent rack 303 contains a number of reagents. The reagents currently used comprise 90 stock solutions, divided into 5 groups: precipitant, buffer, pH, additive and detergent. The concentrations and pHs of the stock solutions are chosen within the user-defined ranges. It is understood that system may contain fewer or more reagents and that the types of reagents may be varied.

The recipe mixer 302 program output contains specific information about the location and volume of all reagents in reagent rack 303 to be aspirated by the recipe mixer 302 and the destination for dispense. The recipe mixer has been programmed to handle the run time instructions supplied by computer and liquid class predictor 311. The robot instructions consist of a series of stand-alone procedures customized to handle various stock-solution viscosity ranges by reading in the corresponding robot "performance" file but also by adjusting flush/wash cycles. The information in the performance files comprises variables such as volume dependent aspiration and dispense speeds, air gaps, delay times, etc.

The reagents are held on the stock reagent rack 303 in a stainless steel metal rack with a footprint to fit on the robot deck. This rack can hold more than 100 stock solutions of 50, 15 and 5 ml vials, depending on the frequency of use for each stock solution. The recipe mixer 302 is "trained" on the rack specifications for each vial position. With this embodiment's current implementation a CRYSTOOL-Screen consisting of 1 ml each of 96 conditions is dispensed in to a 96-well deep-well plate in under 3 hours.

The recipe mixer 302 sets up completed crystallization experiments into 96-well sitting drop plates, bioblock 304, by simple mother-daughter-transfer from a premixed screen and a 1 to 96 well transfer of protein stock solution. There is sufficient reagent for setting up crystallization experiments for four proteins from one deep-well plate with a total setup time of ~10 min per protein per plate. The reagent mixes in bioblock 304 are purely random. The inherent efficiency of random screening techniques has been demonstrated by applicants.

The recipe mixer 302 allows custom labware and integration with other automated devices. The recipe mixer 302 has 8 independent washable tips that can pipette volumes from 1 ul to 1 ml. The tips are washable, stainless steel and Teflon®-coated. Built in liquid-level-sensing technology performs down to 50 µl and can sense both ionic and non-ionic liquids. The tips can spread from 9 mm to 20 mm and automatic computer controlled variable sample probe spacing is provided to accommodate the labware and methodologies. Routine procedures provide cross-contamination control of the sampling tips with in- and external washing via a peristaltic pump. The system is controlled by WinPREP® applications software (under Windows NT®), a graphical user interface that allows programming of liquid-handling protocols and allows the user to directly import text—and comma delimited files as well as interpretable MSL—(MultiPROBE Script Language) or C++—scripts.

The bioblock 304 is initially in place in the recipe mixer 302 as shown in FIG. 3. The central robot machine transfers the bioblock 304 from the recipe mixer 302 to the liquid handling robot 305. A second bioblock 304' is shown in place in the liquid handling robot 305. This illustrates the central robot machine transferring a bioblock from the recipe mixer 302 to the liquid handling robot 305.

The liquid handling robot 305 utilizes samples from the sample containing unit 306 and reagent mixes form the bioblock 304' to place samples in the 96 position crystallization plate 307. The liquid handling robot 305 sets up completed crystallization experiments into 96-well sitting drop plates, bioblock 304', by simple mother-daughter-transfer from a premixed screen and a 1 to 96 well transfer of protein stock solution.

The crystallization plate 307 is moved to platesealer robot 308 by the central robot machine 301. The 96 well crystallization plate 307 is sealed with clear film. The crystallization plate 307 is moved to an incubation unit 309 by the central robot machine 301. The incubation unit may be refrigerated and the crystallization plate 307 is incubated long enough to allow crystals to form. The platesealer robot 308 and incubation unit 309 are well know in the art and may be commercially available units.

The computer identifies the wells in the crystallization plate 307 that have the most promising crystals. Computer systems for analyzing images are well known in the art. The computer and liquid class predictor 311 analyzes the results of images of the crystals that have been formed in the crystallization plate 307 and establishes a new set of test specifications. The new set of specifications are used for another crystallization experiment by processing in the manner previously explained; however, instead of starting with purely random reagent mixes in bioblock 304, the mixes are produced according to the new set of specifications.

Figure 4:
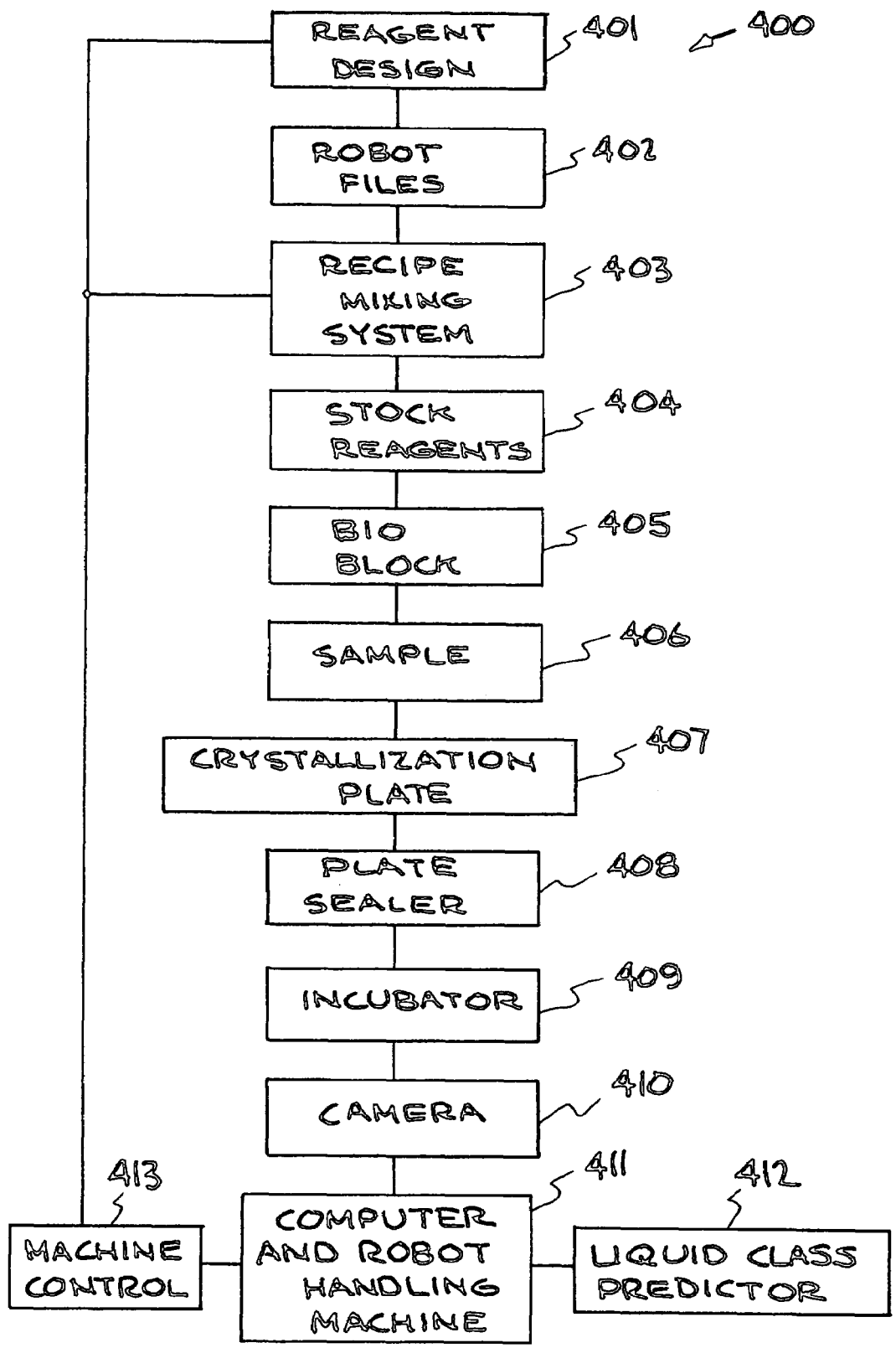
FIG. 4 illustrates yet another embodiment of a liquid class predictor system for establishing liquid classes of complex mixtures for liquid handling equipment constructed in accordance with the present invention.

Referring now to FIG. 4, yet another embodiment of a liquid class predictor system for establishing liquid classes of complex mixtures for liquid handling equipment constructed in accordance with the present invention is illustrated. This embodiment of a liquid class predictor system is part of an automated system for sustainable high-throughput crystallization screening. The automated system for sustainable high-throughput crystallization screening is designated generally by the reference numeral 400.

As illustrated in FIG. 4, a computer and robot handling machine 411 provides reagent design 401 and controls a recipe mixing system 403. The computer and robot handling machine 411 controls the recipe mixing system 403, moves the bio block 405 containing the recipes of reagents and the sample 406 to the crystallization plate 407.

A liquid class predictor 412 is connected to the machine control system 413 and the computer and robot handling machine 411. The machine control system 413 enables the computer and robot handling machine 411 to adjust for the complex mixture represented by the specific recipe. This allows the computer and robot handling machine 411 to use recipe mixtures with a wide range of viscosities so they can be dispensed with high precision.

The computer and robot handling machine 411 handles recipe mixtures with a wide range of viscosities. The performance of most liquid handling equipment is highly sensitive to the physical properties of liquids being handled and must be carefully calibrated for to maintain precision. Machine calibration becomes impractical if the number of reagents becomes very large. Tuning instrument performance and assigning the correct machine parameters for each complex mixture of reagents generated from combinatorial matrices of liquids quickly becomes prohibitive given the number of possible combinations in complex mixtures.

The reagent design 401 is used to create a set of robot files 402. The reagent design is used by a recipe mixing system 403 to randomly select reagent components from a set of stock reagents 404 and create a multiplicity of reagent mixes in bioblock 405. The initial reagent design is a purely random reagent design.

Sample 406 and bioblock 405 are used with a crystallization plate 407 to create a multiplicity of individual analysis plates within crystallization plate 407 wherein each of the analysis plates receives a set format of the reagent mixes combined with the sample. The crystallization plate 407 is sealed by plate sealer 408 and transferred to an incubator 409 for incubation. Incubation promotes growth of crystals in the analysis plates.

A camera 410 is used to create images of the crystals in the analysis plates. A computer and robot handling machine 411 analyzes the images with regard to suitability of the crystals for analysis by x-ray crystallography. The computer and robot handling machine 411 provides a reagent mix design that produces specific reagent mixes that are expected to produce the best crystals for analysis by x-ray crystallography.

The reagent mix design is used to create a second multiplicity of mixes of the reagent components. The second multiplicity of reagent mixes are used for another round of automated macromolecular crystallization screening the sample. The second round of automated macromolecular crystallization screening may produce crystals that are suitable for x-ray crystallography. If the second round of crystallization screening does not produce crystals suitable for x-ray crystallography a third reagent mix design is created and analyzed according to the method.

In the human genome for, e.g., the estimated total number of 26,000 to 38,000 protein coding genes (Venter et al., 2001) is expected to be exceeded by the number of actually expressed proteins by an order of magnitude (believed to be more than a million) as a result of splice variants, posttranslational modifications, etc. To meet the challenge of proteomics, several large-scale structural genomic projects have been initiated. In the United States alone the Protein Structure Initiative (PSI) of the National Institute of General Medical Sciences (NIGMS) and the National Institute of Allergy and Infectious Disease (NIAID) has launched nine structural genomics centers. Their efforts focus on obtaining atomic-resolution 3-D protein structures of whole genomes that will ultimately represent all domain folds present in the biosphere and provide representative structures for all individual protein families.

One of the major bottlenecks in order to reach the capacity necessary for large-scale structure determination is the availability of highly diffracting protein crystals. The most promising way to increase the rate of determined protein structures is the automated performance of a large number of crystallization trials to meet this demand in protein crystallization.

Applicants have demonstrated advantages of random screening techniques. Applicants have generated any number of random combinations of crystallization conditions from a large set of starting stock-solutions and have interfaced the random screening to an automated liquid-handling system. The liquid-handling system allows for random access pipetting of stock-solutions with aspiration and dispense speeds tuned for stock-solution viscosities over a range of volumes (5 ul-3 ml). All necessary parameters for setup of a fully customizable set of crystallization experiments are supplied at run time; machine performance related parameters are preprogrammed into the setup protocol. A thorough screen for one protein consists of 288 experiments, based on the preposition that the crystallization success rate for most proteins is 2% or higher. One ml of a full screen is pipetted into three 96-well plates in under 3 h. Throughput is estimated at 10 plates per day yielding 960 different crystallization experiments.

Using 90 stock solutions, the system can generate over 30 million unique experiments. Mixing only 96 of these experiments from pre-made stock solutions by hand takes about 12 hours. Therefore clearly setting up of experiments at a larger scale can only be achieved by using automated devices. A fully customizable program that will generate over 30 million random combinations of crystallization conditions has been produced. The set of precipitants, additives and buffers in various concentration and pH ranges used currently consists of 90 manually premixed stock solutions. The worksheet lists all of the available stock solutions, divided into 5 groups: precipitant, buffer, pH, additive and detergent. The concentrations and pHs of the stock solutions are listed indicating the minimal and maximal possible range. The system has a default frequency assigned to each stock solution. Changes in frequency of each stock solution to individual preferences are automatically adjusted over each particular group whenever the worksheet is edited. After entering the number of experiments to be generated and the desired volume for each condition, the edited worksheet is executed and saved. The system generates an experiment list that lists used stock solutions with concentrations used (in Units of % or molarities) and pH if a buffer was allocated to the particular condition. The system also calculates the amount to be used of each premixed stock solution.

The system is interfaced with a liquid-handling robot system. An automated liquid-handling application demands the operating criteria of customizable functionality and programming flexibility of the system. Tip technology has to encompass independent controllable tips with variable tip movement and separation for a wide dynamic range of volume dispensing (milliliters to microliters) and include carry-over elimination. Further essential capabilities of a robotic pipettor are handling of data files and executable programs as user input.

The system has 8 independent washable tips that can pipette volumes from 1 ul to 1 ml. The tips are washable, stainless steel and Teflon®-coated. Built in liquid-level-sensing technology performs down to 50 µl and can sense both ionic and non-ionic liquids. Varispan™ Variable Tip Separation allows the tips to spread from 9 mm to 20 mm and provides automatic computer controlled variable sample probe spacing to accommodate our custom labware and methodologies. Routine procedures provide cross-contamination control of the sampling tips with in- and external washing via a peristaltic pump: The system is controlled by WinPREP® applications software (under Windows NT®), a graphical user interface that allows programming of liquid-handling protocols and allows the user to directly import text- and comma delimited files as well as interpretable MSL—(MultiPROBE Script Language) or C++—scripts.

Ninety vials of different sizes holding three types volumes: 50 ml, 15 ml and 5 ml are used. A stain-less steel rack holding up to 100 vials fits on the robot deck. Dependent on the frequency of use each stock solution was assigned a vial with an appropriate volume to allow for continuous processing. With WinPREP, the rack itself and each position in it were defined regarding their X, Y and Z coordinates into a labware called CS_rack. Accordingly, aspirate and dispense heights, travel and search height of the tips are specified. Ninety plates with SDS-footprint are commercially available and fit into the support tiles on the robot deck.

A Millipore Analyzer Feed System AFS-18D is used to provide the MultiPROBE II HT with distilled and degassed water that is used as system liquid. This system filters tap water to consistently-pure, reagent-grade Type I water with a final resistivity of >-cm and ●=10 M bacteria of <=10 cfu/mL at a flow rates of 3-90 L/hr. It further incorporates Millipore's patented degassing technology for removal of dissolved gases (<=3.5 ppm dissolved oxygen) from the final product water.

A component of the interface is the output of the experiments in robot format in combination with a customized liquid-handling protocol programmed in WinPREP application software. Within WinPREP a liquid-handling protocol had to be developed that would create a procedure that would: read in text-files, randomly aspirate various volumes of stock solutions from the CS_rack, randomly dispense them into the according well of 96-well Marsh plates, adapt aspiration and dispense performance for different stock solution viscosities, and eliminate cross-contamination by sufficient wash procedures.

All stock solution are categorized into 4 classes of viscosities: alcohols (A), low viscosity (L), high viscosity (H) and watery solutions (W). Alcohols were easy to identify (Ethanol, 2-Buthanol, Methanol, MPD, Hexandiol, Isopropanol) and teamed up with DMSO. Lower PEGs from 400 to 2000 as well as almost all detergents were categorized as low viscosity. High viscosity are PEGs 5000 and higher as well as glycerol. The category of aqueous solutions comprises all buffers, salts and EDTA.

The WinPREP software uses so called Performance Files, which utilize specific accuracy calibration and settings for aspirate and dispense speeds, waste volumes, transport and system air gaps, blowout volumes, blowout delays, and waste volumes. Three new performance files optimize pipetting precision and accuracy for the stock solutions of each of the 4 viscosities. For water and watery solutions a WinPREP default Performance File is used. Performance testing was completed on the MultiPROBE II HT and MultiPROBE II systems with WinPREP software.

A separate procedure was created in WinPREP, sorted according to the volatility of the stock solutions. The program starts with the dispense of water. Since the Millipore Analyzer Feed System provides extremely pure and degassed water, the system liquid is used for the required amounts of water in the CRYSTOOL experiments. Subsequently, the procedures for aqueous solutions, low viscosity, high viscosity and finally alcohols are completed to allow for minimum evaporation time. The defined Labware (CS_rack and Marsh plates) are mapped (assigned a specific position on the robot deck with the graphical user interface of WinPREP) and named once and is valid for all subsequent procedures.

To eliminate cross-contamination volumes of wash liquid have been determined for each viscosity group. This is accomplished by adding 10 μl of highly concentrated blue dye to stock solutions and measuring respective absorbances at 631 nm. Subsequently 1 ml of each solution was pipetted with the Packard MP II HP. After flushing and washing the tips the same stock solution was pipetted without dye 10 times. For each pipetting cycle 0.5 ml of dispensed stock solution was collected and spectroscopically tested for remnants of the dye at 631 nm. Different wash volumes were tested and evaluated. For every WinPREP procedure the lowest wash volume without measurable traces of contamination was determined and incorporated.

Programming the liquid-handling protocol assigns each procedure its specific "Robot file": a comma delimited output generated that includes pipetting volumes, source and destination identifiers and positionings. WinPREP reads these 5 files on run-time and converts the comma delimited file into a column-based spread-sheet. Every single column now has to be mapped correctly within the WinPREP procedure. Fortunately, upon replacing a file with another the program remembers the mapping, so it only has to be set up once, given that always the same file-format is used.

An output file format is used that can be read and interpreted by the MultiPROBE. The software structure of WinPREP suggested a comma delimited file was the format that could be easily generated by CRYSTOOL. A total of five files needed to be generated for each viscosity and the water procedure in the liquid-handling protocol.

First, a number was assigned to each stock reagent in strict correspondence to the positioning in the CS_rack. The previously used name of each stock reagent was then replaced by its number. The number of each stock reagent equals the source position and the source identifier for all source positions is CS_rack (since only one rack is used). The system was then programmed to split all generated experiments into single components with their respective volumes. For the destination identifier, the first 96 experiments were assigned to MarshPlate 1 the second to MarshPlate 2, etc. The destination positioning was assigned column wise (given by the fastest mechanical pipetting process) to each plate identifier. Each line in the generated file now corresponds to information about the destiny of a single stock solution. To be able to sort by viscosities, viscosity flags (A, L, H or W) were added to all stock solutions within the worksheet. Finally the whole experiment list is sorted and divided by viscosities (and water) resulting in the output of 5 comma delimited text files that can be directly supplied to the liquid-handling protocol of the MP II.

After automated pipetting is finished, the plates are sealed manually with Epoxyclear Adhesive Film from Hampton. Mixing of the components is achieved by manually inverting and shaking the sealed plates a couple of times. Bubbles and foaming that can occur due to mixing are eliminated by centrifuging. The crystallization plate is transferred to an incubator for incubation. Incubation promotes growth of crystals in the analysis plates.

A camera is used to create images of the crystals in the analysis plates. A computer analyzes the images with regard to suitability of the crystals for analysis by x-ray crystallography. The computer and robot handling machine provides a reagent mix design that produces specific reagent mixes that are expected to produce the best crystals for analysis by x-ray crystallography. The reagent mix design is used to create a second multiplicity of mixes of the reagent components. The second multiplicity of reagent mixes are used for another round of automated macromolecular crystallization screening the sample. The second round of automated macromolecular crystallization screening may produce crystals that are suitable for x-ray crystallography. If the second round of crystallization screening does not produce crystals suitable for x-ray crystallography, a third reagent mix design is created and analyzed. If necessary, additional reagent mix designs are created and analyzed.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for providing liquid mixtures for crystallization screening, comprising:
 a recipe mixer,
 a stock reagent rack,
 a bioblock,
 a sample container,
 a crystallization plate,
 a late sealer robot,
 an incubator unit, a liquid handling robot connected to said stock reagent rack, said bioblock, said sample container, and said crystallization plate, a liquid class predictor connected to said recipe mixer, and a machine control system connected to said liquid handling robot, said plate sealer robot, said recipe mixer, and said liquid class predictor.

2. The apparatus for providing liquid mixtures for crystallization screening of claim 1 wherein said recipe mixer is a recipe mixer that produces specific recipes from said stock reagent rack that will be used by said liquid handling robot.

3. The apparatus for providing liquid mixtures for crystallization screening of claim 2 wherein said liquid class predictor is a liquid class predictor that determines the liquid classes of said specific recipes produced by said recipe mixer and produces liquid class information.

4. The apparatus for providing liquid mixtures for crystallization screening of claim 3 wherein said liquid class predictor is a liquid class predictor that provides said liquid class information to said machine control system.

5. The apparatus for providing liquid mixtures for crystallization screening of claim 1 including a camera operably connected to said crystallization plate.

6. An apparatus for growing crystals and sustainable high-throughput crystallization screening of the crystals, comprising:

a recipe mixing system for mixing individual recipes of complex liquid mixtures for the crystals, a reagent design unit connected to said recipe mixing system for creating a set of robot files for said individual recipes of said complex liquid mixtures, stock reagents, a bio block, a crystallization plate, a plate sealer, an incubator, a robot handling machine connected to said stock reagents, said bio block, said crystallization plate, said plate sealer, and said incubator, a machine control system connected to said recipe mixing system, said reagent design unit, and said robot handling machine to instruct the robot handling machine for growing the crystals and screening of the crystals, and a liquid class predictor connected to said machine control system for adjusting said individual recipes.

7. The apparatus of claim 6 wherein said liquid class predictor for adjusting said individual recipes is a liquid class predictor for adjusting said individual recipes from reagents with known response curves.

8. The apparatus of claim 6 wherein said step of predicting liquid classes produces liquid class information and said liquid class information is used to instruct the liquid handling equipment including a camera operably connected to said incubator for creating images of the crystals.

9. A method of growing crystals and screening the crystals by establishing liquid classes of mixtures for a robot handling machine, said mixtures composed of components, comprising the steps of:

preparing a response curve for said components, using said response curve to prepare a response indicator for said mixtures, and deriving a model that relates said components and said mixtures to establish said liquid classes, using said robot handling machine and said liquid classes for mixing individual recipes of the mixtures for the crystals, using said robot handling machine and an incubator for incubating said individual recipes of the mixtures for the crystals, and screening the crystals.

10. The method of growing crystals and screening the crystals of claim 9 wherein said step of deriving a model comprises empirically deriving a model by linear regression.

11. The method of growing crystals and screening the crystals of claim 9 including the steps of preparing a working set of mixed cocktails from said components with known response curves and measuring the volume dispensed vs. expected volume of water dispensed with said equipment parameters.

* * * * *